(12) United States Patent
Legeay et al.

(10) Patent No.: US 9,005,960 B2
(45) Date of Patent: Apr. 14, 2015

(54) FUNCTIONALIZED MEMBRANE FOR A CHAMBER FOR ENCAPSULATING CELLS PRODUCING AT LEAST ONE SUBSTANCE OF THERAPEUTIC INTEREST AND BIOARTIFICIAL ORGAN COMPRISING SUCH A MEMBRANE

(75) Inventors: Gilbert Legeay, Saint Saturnin (FR); Séverine Sigrist, Benfeld (FR); Arnaud Coudreuse, Le Mans (FR)

(73) Assignees: Association pour les Transferts de Technologie du Mans, Le Mans (FR); Centre Europeen d'Etude du Diabete, Strasbourg (FR)

( * ) Notice: Subject to any disclaimer, the term of this patent is extended or adjusted under 35 U.S.C. 154(b) by 0 days.

(21) Appl. No.: 13/701,750

(22) PCT Filed: May 31, 2011

(86) PCT No.: PCT/IB2011/052391
§ 371 (c)(1),
(2), (4) Date: Feb. 5, 2013

(87) PCT Pub. No.: WO2012/017337
PCT Pub. Date: Feb. 9, 2012

(65) Prior Publication Data
US 2013/0131828 A1    May 23, 2013

(30) Foreign Application Priority Data

Jun. 4, 2010    (FR) .................................... 10 02371

(51) Int. Cl.
*C12M 1/12*    (2006.01)
*A61F 2/02*    (2006.01)
(Continued)

(52) U.S. Cl.
CPC . *A61F 2/02* (2013.01); *A61L 27/54* (2013.01); *A61L 33/0005* (2013.01);
(Continued)

(58) Field of Classification Search
CPC ..... A61K 9/0024; A61K 9/0004; A61L 31/10
USPC .............. 623/64, 71, 72, 73, 74, 75; 424/422, 424/424, 473; 435/295.3
See application file for complete search history.

(56) References Cited

U.S. PATENT DOCUMENTS 4,323,457 A    4/1982    Sun et al.
4,578,191 A    3/1986    Jaffrin et al.
(Continued)

FOREIGN PATENT DOCUMENTS

WO    WO 90/15863 A1    12/1990
WO    WO 93/03768 A1    3/1993
(Continued)

OTHER PUBLICATIONS

Sudebi D.P. Contact Angle Measurement for the Surface Characterization of Solids. The Himalayan Physics. vol. II. May 2011.pp. 1-4.*
(Continued)

*Primary Examiner* — Thomas J Sweet
*Assistant Examiner* — Rokhaya Diop
(74) *Attorney, Agent, or Firm* — Alston & Bird LLP (57) ABSTRACT

The present invention relates to a functionalized semi-permeable membrane composed of a porous biocompatible support pretreated so as to increase the surface energy thereof and characterized in that it includes at least two layers, each having a hydrophilic polymer and at least one biological active molecule, and to the use thereof in particular for producing a bioartificial organ.

9 Claims, 4 Drawing Sheets (51) Int. Cl.
*A61L 27/54* (2006.01)
*A61L 33/00* (2006.01)
*B01D 67/00* (2006.01)
*B01D 69/10* (2006.01)
*B01D 69/12* (2006.01)
*B01D 69/14* (2006.01)

(52) U.S. Cl.
CPC ......... *B01D 67/0088* (2013.01); *B01D 67/009* (2013.01); *B01D 67/0093* (2013.01); *B01D 69/105* (2013.01); *B01D 69/12* (2013.01); *B01D 69/144* (2013.01)

(56) References Cited

U.S. PATENT DOCUMENTS

| | | | |
|---|---|---|---|
| 4,956,219 | A | 9/1990 | Legras et al. |
| 5,262,055 | A | 11/1993 | Bae et al. |
| 5,605,835 | A | 2/1997 | Hu et al. |
| 5,837,234 | A | 11/1998 | Gentile et al. |
| 5,981,211 | A | 11/1999 | Hu et al. |
| 6,023,009 | A | 2/2000 | Stegemann et al. |
| 2004/0137063 | A1* | 7/2004 | Legeay et al. ............... 424/473 |
| 2005/0152950 | A1* | 7/2005 | Saffran ........................ 424/424 |
| 2006/0198864 | A1* | 9/2006 | Shults et al. ................ 424/422 |

FOREIGN PATENT DOCUMENTS

| | | |
|---|---|---|
| WO | WO 94/02129 A1 | 2/1994 |
| WO | WO 94/26399 A1 | 11/1994 |
| WO | WO 98/28026 A1 | 7/1998 |
| WO | WO 02/060409 A1 | 8/2002 |

OTHER PUBLICATIONS

International Search Report for Application No. PCT/IB2011/052391 dated Nov. 30, 2011.

International Preliminary Report on Patentability for International Application No. PCT/IB2011/052391 dated Aug. 24, 2012.

J. of Vascular Research, vol. 40, No. 4 (2003) 359-367.

Cell Transplantation, vol. 12, (2003) 627-635.

Ricard, A., *Reactive Plasmad*, SVF Editions (1995).

\* cited by examiner

FUNCTIONALIZED MEMBRANE FOR A CHAMBER FOR ENCAPSULATING CELLS PRODUCING AT LEAST ONE SUBSTANCE OF THERAPEUTIC INTEREST AND BIOARTIFICIAL ORGAN COMPRISING SUCH A MEMBRANE

FIELD

The present invention relates to the field of bioartificial organs that can be implanted in the body of a patient and provided in the form of devices encapsulating cells secreting substances of therapeutic interest.

BACKGROUND

The treatment of pathological conditions requiring a continuous supply to the body of substances of therapeutic interest has made necessary the development of devices which can be implanted in a patient and which are capable of releasing these substances efficiently and sometimes for long periods of time.

To satisfy this need, bioartificial organs have been developed which contain cells producing one or more substances of therapeutic interest. The cells contained in a bioartificial organ are confined in internal spaces, or encapsulation chambers, delimited by at least one semi-permeable membrane. Such a semi-permeable membrane should allow the diffusion of substances of therapeutic interest to the target cells in the patient's body, while being impermeable to the antibodies and cells of the patient's immune system.

The expression artificial organ is understood to mean a device comprising at least one encapsulation chamber consisting of at least one semi-permeable membrane; said encapsulation chamber is intended to contain cells secreting a substance of therapeutic interest.

The substance of therapeutic interest may be a neurotransmitter, a hormone, a growth factor or a cytokine; for example and with no limitation, insulin, growth hormone, calcitonin.

One example of this type of device is described in international application WO 02/060409 which is aimed more particularly at the development of semi-permeable membranes with improved mechanical and selective permeability properties for the production of bioartificial organs consisting of a chamber for encapsulating cells producing an active substance. Implanted in the patient, such a bioartificial organ allows the release of the active substance and the treatment of the patient.

A difficulty encountered during the implantation of this type of device is the relatively short duration of its efficacy which can be explained by a lack of oxygenation of the cells encapsulated in the encapsulation chamber and their inactivation by low molecular weight cytokines produced by the immune cells of the recipient patient.

Sigrist et al. improved the viability of pancreatic islets encapsulated in an encapsulation chamber consisting of a semi-permeable membrane made of sodium polyacrylonitrilemethallylsulfonate ("AN69" membrane from the company HOSPAL) by adding, inside this chamber, the epithelial cell growth factor (VEGF). After implanting in mice a bioartificial organ consisting of the encapsulation chamber thus prepared, the division of VEGF into the tissues surrounding the implant allowed the induction of angiogenesis around the implant (J. of Vascular Research, 2003, 40(4):359-67 and Cell Transplantation, 2003, vol. 12, pp. 627-635).

This technique has however limits linked to the low diffusibility of the VEGF across the walls of the chamber and to the importance of inducing angiogenesis as early as possible after the implantation of the bioartificial organ.

U.S. Pat. No. 5,262,055 provides an artificial pancreas consisting of an encapsulation chamber equipped with an immunoprotective membrane and which contains pancreatic islets in a heat-sensitive polymer matrix; the contents of the encapsulation chamber may be replaced after implantation by means of two fine tubes which connect the inside of the encapsulation chamber to the outside of the patient's body. The immunoprotective nature of the semi-permeable membrane is conferred by the impermeability of the membrane which prevents the entry into the device of cells of the immune system. This patent also proposes the incorporation, into the heat-sensitive polymer matrix, of polymer microparticles allowing the release of active agents intended to induce vascularization or to inhibit macrophage activity around the encapsulation chamber. The double disadvantage of this device is the location of the polymer microparticles inside the encapsulation chamber (low diffusibility of the semi-permeable membrane) and the release and then the undesirable accumulation in the body of the polymer constituting the microparticles during the release of the active agents.

International application WO 94/26399 describes semi-permeable membranes which bear active agents attached by covalent bonds; this type of membrane is however not satisfactory because their preparation requires an additional step of covalent attachment of the active agents and in that the quantity of active agents is limited to that present at the surface of the membrane.

Application US 2006/0198864 describes membranes for biological interfaces intended to cover implanted devices such as probes for measuring blood glucose. These membranes have an architecture in two parts, the supporting layer and the external layer which has a very marked relief (honeycomb architecture having cavities 20 to 1000 μm in size) and which allows the development of blood vessels. This document also describes the possibility of adding active agents to these membranes in particular in order to limit inflammatory manifestations and to promote vascularization; these agents are then either incorporated into the matrix of the membrane (composed of polycarbonate, PVA or cellulose polymers) or adsorbed or linked by covalent bonds at the surface of the membrane. The use of these membranes for the production of probes intended for the detection of substances such as glucose in the body requires a particular relief and high permeability of the membranes; the inventors observed that the particular structure of these membranes, in particular, the fact that their pores are interconnected (which leads to the obstruction of the pores by cells, thus preventing the circulation of the biologically active molecules and of substances of therapeutic interest), that the supporting layer does not have a cut-off that is specifically chosen to ensure selective permeability and that the hydrophobic materials are used for the production of the external layer of these membranes, means that these supports are not compatible with their use for the preparation of a bioartificial organ and for its operation after implantation in an individual.

Accordingly, several difficulties are encountered during the implantation of a bioartificial organ in a recipient patient; in the first place, it will be necessary to avoid or limit (i) the inflammatory reaction of the patient's tissues caused by the fitting of the bioartificial organ and (ii) the introduction into the reaction chamber of cytokines and chemokines which would destroy the secretory cells. In addition, oxygenation of the secretory cells encapsulated into the bioartificial organ and optimum diffusion of the substance of therapeutic interest into the body require vascularization of the tissues surrounding the bioartificial organ. It is still therefore necessary to improve the properties of the membranes used for the production of bioartificial organs in order to accelerate the implantation and the initiation of operation (secretion of substances of therapeutic interest) of said bioartificial organs in the body of patients.

SUMMARY

The inventors have developed a new type of semi-permeable membranes functionalized with at least two biologically active molecules; said membranes being useful for the production of a bioartificial organ.

A semi-permeable membrane is said to be functionalized when it contains a biologically active molecule whose release in vivo facilitates the implantation and improves the operation of the bioartificial organ.

The inventors have shown that the implantation of bioartificial organs composed of a semi-permeable membrane functionalized with heparin and VEGF as biologically active molecules made it possible to avoid an inflammatory reaction around the bioartificial organ and led to the development of blood vessels around the bioartificial organ after only two weeks; such a vascularization being observed only after two months for bioartificial organs whose semi-permeable membranes are not functionalized.

The present invention thus relates to a functionalized semi-permeable membrane composed of a porous biocompatible support pretreated so as to increase the surface energy thereof and characterized in that it also comprises at least two layers, each comprising a hydrophilic polymer and at least one biologically active molecule.

More particularly, this is a functionalized semi-permeable membrane composed of a porous biocompatible support, characterized in that:
  said porous biocompatible support is pretreated so that its surface energy is greater than or equal to 50 mJ·m$^{-2}$;
  the pores of said porous biocompatible support have an inner size between 5 and 100 nm, and
  said functionalized semi-permeable membrane comprises at least two layers each comprising a hydrophilic polymer and at least one biologically active molecule.

The preparation of the biocompatible support may be carried out according to the method described in international application WO 02/060409.

The biocompatible support consists of porous polycarbonate or polyester or polyethylenimine; its thickness is between 5 and 100 μm, preferably between 10 and 60 μm. The formation of the pores may be carried out by electron bombardment or by heavy ion bombardment; this second method is in particular described in U.S. Pat. No. 4,956,219. In the case of a heavy ion bombardment, the density of the heavy ions bombarded at the surface of the biocompatible support determines the density of the pores, whereas the chemical erosion treatment time determines the size of the pores.

In the context of the present invention, the pores made on the biocompatible support have an inner size between 5 and 100 nanometers, preferably between 5 and 50 nanometers.

The surface of the porous biocompatible support is then treated so as to increase the surface energy thereof. The treatment of the support leads to the creation of polar sites at the surface of the porous biocompatible support, in particular the treatment causes an increase in the proportion of carbonyl, hydroxy or amine groups, and of free radicals. The free radicals combine with each other, or with atmospheric oxygen, thus creating polar sites.

It is thought that a sufficient surface energy is such that the angle of contact measured between the tangent of a drop of water placed on the support and the surface of the membrane is less than 40°; which corresponds to a surface energy of at least 50 mJ·m$^{-2}$.

Thus, the objective of the treatment of the support is to obtain a surface energy greater than or equal to 50 mJ·m$^{-2}$.

The wetting and surface energy values which follow are given by way of example:
1) Untreated Polycarbonate Support:
wetting angle (water): 60°;
surface energy: 41 to 44 mJ·m$^{-2}$ (polar component: 15 mJ·m$^{-2}$)
2) Plasma-treated Polycarbonate Support:
wetting angle (water): 25°;
surface energy: 66 mJ·m$^{-2}$ (polar component: 37.2 mJ·m$^{-2}$)
3) Plasma-Treated Polycarbonate Support Covered with a Hydrophilic Layer:
wetting angle (water): 20°
surface energy: 66.7 mJ·m$^{-2}$ (polar component: 40 mJ·m$^{-2}$)

In particular, in the case of a biocompatible support made of polycarbonate, the polar sites present at the surface of the biocompatible support constituting the semi-permeable membrane of the invention comprise the following sites: $CH_3O$, $C_2H_3O$, $C_3H_3O$, $C_3H_7O$, O, OH, $C_2OH$, $C_8H_5O$, $NH_4^+$, $C_2H_8N^+$, R—OH (alcohol), $(R)_3$—NH (amine) and R—CO—NH (amide), in which the substituent R represents a constituent radical of the polycarbonate polymer of the biocompatible support. These polar sites increase the surface energy of the biocompatible support and thus allow the adhesion of the layers of hydrophilic polymer.

Preferably, the creation of polar sites at the surface of the biocompatible support is carried out by plasma treatment, corona discharge or by electromagnetic discharge at atmospheric pressure or under vacuum.

For example, the support is argon radiofrequency plasma-treated. It may be treated at a plasma reactor emission power between 2 and 10 watts per liter of reactor capacity, between 1 and 30 minutes. The treatment may also be carried out by microwave plasma, at the same power, but for 5 seconds to 20 minutes.

Preferably, the plasma treatment is carried out under vacuum.

For the implementation of a plasma treatment method, reference may be advantageously made by persons skilled in the art to the manual by A. Ricard ("Reactive plasmas", SVF editions, 1995).

The treatment may also be carried out by corona discharge. The treatment voltage is advantageously between 50 and 500 volts, the intensity being variable according to the treatment device and the supports treated.

The corona discharge treatment may be carried out with the aid of devices with opposite parallel electrodes, with adjacent parallel electrodes (electrode arc of about 5 mm in height), or with a blown arc (adjacent parallel electrodes with a gas stream between them, thus creating an electric arc of about 10 cm in height).

For the implementation of a corona discharge or electromagnetic discharge treatment method, reference may be advantageously made by persons skilled in the art to the manual by A. Ricard (1995).

The duration of treatment is of the order of a few tenths of a second, preferably between 0.1 and 1 second. In the event of a continuous treatment, the duration of exposure is such that the material to be treated passes through the treatment device at a speed of a few centimeters to several decimeters per second.

In addition, the biocompatible support may be treated several times in order to increase the efficiency of the treatment.

Most preferably and in the case of a biocompatible support made of polycarbonate, the creation of polar sites is carried out by an argon plasma treatment step in a 20 liter Branson RF type reactor performed at a power of 50 watts for ten minutes. In this particular embodiment, there was observed at the surface of the biocompatible support made of polycarbonate, by measurement by secondary ion mass spectrometry, the following composition, as polar sites, quantified by the intensity of the secondary ions detected at the following mass/charge (m/z) ratios:

in positive mode: 31 ($CH_3O$), 43 ($C_2H_3O$), 55 ($C_3H_3O$), 59 ($C_3H_7O$), 18 ($NH_4^+$) and 46 ($C_2H_8N^+$); and in negative mode: 16 (O), 17 (OH), 41 ($C_2OH$), 117 ($C_8H_5O$).

According to the invention, each layer of hydrophilic polymer comprising at least one biologically active molecule has a thickness between 10 and 1000 nano-meters, preferably between 10 and 100 nanometers and most preferably between 10 and 50 nanometers.

In the context of the present invention, the expression hydrophilic polymer is understood to mean a polymer which, when applied to a porous biocompatible support, is such that a drop of water deposited on said polymer has an angle value less than 25°, preferably less than 22° after measurement according to the "sessile drop" test as described in international application WO 02/060409.

Preferably, the hydrophilic polymer is soluble in water. Indeed, because of the implantation of the bioartificial organ in the body of a host organism, the use of organic solvents is not recommended because their complete removal is difficult and their presence, even in small quantities, is not compatible with a therapeutic or surgical use in humans or animals.

The hydrophilic polymer is preferably chosen from the following polymers:

cellulose compounds, such as ethyl cellulose (EC), hydroxypropyl methylcellulose (HPMC), for example HPMC E4M marketed by the company DOW CHEMICALS, or the one called Aqualon marketed by the company Hercules, or carboxymethylcellulose (CMC) marketed by the company Hercules;

polyacrylamides and their copolymers, such as those marketed by the company SIGMA (UPSALA, Sweden);

polyvinylpyrrolidone (PVP) and its copolymers, such as those marketed by the company BASF, such as Kollidon (K30, K90);

polyvinyl alcohols;

copolymers of vinyl acetate, such as the copolymer of polyvinyl acetate and polyvinyl alcohol marketed under the name Mowiol by the company HOECHST;

polyethylene glycols, such as those marketed by the company SIGMA;

polypropylene glycols;

hydrophilic poly(meth)acrylates, such as those marketed by the company DEGALAN or DEGUSSA;

polysaccharides;

hyaluronic acid-based polymers;

chitosans, such as those marketed by the company SIGMA.

Preferably, the hydrophilic polymer is chosen from cellulose compounds, in particular HPMC, EC or CMC, polyvinylpyrrolidones, polyvinyl alcohols and some polyacrylates such as poly(hydroxyethyl acrylate) (HEMA) or copolymers of acrylic acid.

The hydrophilic polymer which can be used according to the invention may also be composed of a mixture of two or more hydrophilic polymers mentioned above, for example HPMC and CMC, HPMC and EC, and the like.

The biologically active molecule is mixed with the hydrophilic polymer and is intended to be released into the medium surrounding the semi-permeable membrane so as to induce a response of the tissue(s) of the patient receiving the bioartificial organ.

The response of the tissue which it is desired to induce may be of several types; in general, the biologically active molecules which may be introduced into the functionalized semi-permeable membranes according to the invention are chosen from anti-inflammatory agents, anti-infective agents, anesthetics, growth factors, angiogenesis-stimulating and/or vascularization-inducing agents, wound-healing agents, immunosuppressive agents, antithrombotic agents including antiaggregation agents and anticoagulating agents, inhibitors of angiotensin-converting enzyme (ACE), or molecules stimulating insulin secretion (IGF, glucagon-like peptide 1 (GLP-1) or its derivatives, incretin mimetics).

Among the anti-inflammatory agents, mention may be made of nonsteroidal anti-inflammatory drugs (NSAIDs) such as acetaminophen, aminosalicylic acid, aspirin, celecoxib, choline magnesium trisalicylate, declofenac, diflunisal, etodolac, flurbiprofen, ibuprofen, indometacin, interleukin IL-10, IL-6 mutein, anti-IL-6, NO synthase inhibitors (for example L-NAME or L-NMDA), interferon, ketoprofen, ketorolac, leflunomide, mefenamic acid, mycophenolic acid, mizoribine, nabumetone, naproxen, oxaprozin, piroxicam, rofecoxib, salsalate, sulindac, and tolmetin and corticoids such as cortisone, hydrocortisone, methylprednisolone, prednisone, prednisolone, betamethasone, betamethasone dipropionate, betamethasone valerate, beclomethasone dipropionate, budesonide, dexamethasone sodium phosphate, flunisolide, fluticasone propionate, paclitaxel, tacrolimus, tranilast, triamcinolone acetonide, fluocinolone acetonide, fluocinonide, desonide, desoximetasone, fluocinolone, triamcinolone, triamcinolone, clobetasol propionate, and dexamethasone.

The use of antithrombotic agents such as antiaggregation agents (acetylsalicylic acid, clopidogrel, ticlopidine, dipyridamole, abciximab, eptifibatide and tirofiban), anticoagulants (heparin, bivalirudin, dabigatran, lepirudin, fondaparinux, rivaroxaban, epoprostenol, warfarin, phenprocoumone, protein C, drotrecogin alfa, antithrombin, pentosan) and thrombolytic agents (alteplase, urokinase, tenecteplase and reteplase) is preferred.

The preferred antithrombotic agent is heparin.

In addition, it is advantageous to use, as biologically active molecule, a molecule allowing satisfactory vascularization of the tissues surrounding the bioartificial organ; this may be in particular growth factors such as:

those of the PDGF (Platelet derived growth factor) family: PDGF1, PDGF2, VEGF (vascular growth factor), VPF (vascular permeability factor);

those of the EGF (Epidermal Growth Factor) family: EGF, urogastrone (URO) TGFα (Transforming Growth Factor α), amphiregulin;

those of the FGF (Fibroblast Growth Factor) family: numbered 1 to 6, and which may be complexed with heparin;

those of the insulin family: IGF-1 and IGF-2;

neurotrophic factors (NGF);

connective tissue growth factor (CTGF);

hepatocyte growth factors (HGF).

Preferably, they are cell growth factors which promote vascularization by the induction of angiogenesis such as basic fibroblasts growth factor (bFGF), vascular endothelium growth factor (VEGF), platelet-derived endothelial cell growth factor (PDGF1 or 2) or hepatocyte growth factor (HGF).

For the preparation of the layer of hydrophilic polymer and biologically active molecule, the hydrophilic polymer or the mixture of hydrophilic polymers is dissolved in water.

Regardless of the hydrophilic polymer, or mixture of hydrophilic polymers, used, its quantity by total weight of the solution is preferably adjusted so as to obtain an aqueous solution of hydrophilic polymer having a viscosity of between 1 and 10 centipoises.

For example, a viscosity value of the order of 5 to 10 centipoises (cPs) is obtained for an aqueous solution having a concentration of 1% by weight of PVP (Kollidon K90 marketed by the company BASF) or an aqueous solution having a concentration of 0.2% by weight of HPMC (E4M marketed by DOW CHEMICALS). The measurements of viscosity are carried out with the aid of a DIN 30D type needle, at room temperature and for a speed of rotation of 300 to 500 rpm.

Accordingly, by way of illustration, when the hydrophilic polymer is hydroxypropyl methylcellulose (HPMC), polyvinylpyrrolidone (PVP) or a mixture of these two polymers, the percentage by weight of the hydrophilic polymer, relative to the total weight of the aqueous solution of polymer, is advantageously between 0.1% and 1%.

The biologically active molecule is then added to this aqueous solution of hydrophilic polymer and then solubilized or suspended by stirring with a biologically active molecule/hydrophilic polymer ratio between 25/100 and 75/100 by weight, preferably this ratio is between 25/100 and 50/100, the ratio is preferably 25/100 regardless of the biologically active molecule and the hydrophilic polymer.

The application of the layers of hydrophilic polymer and bioactive molecule on the biocompatible support may be carried out by immersion.

Most preferably, the duration of the immersion step is between 5 seconds and 10 minutes.

Advantageously, the immersion step takes place at a temperature between 15° C. and 25° C.

The duration of the step for immersing the biocompatible support in a solution of hydrophilic polymer is adjusted so as to obtain a polymer layer having a thickness between 10 and 1000 nanometers, preferably between 10 and 100 nanometers and most preferably between 10 and 50 nanometers.

Each of the next layers of hydrophilic polymer and biologically active molecule is prepared according to this same method after completely drying the previous layer. It is also possible to prepare a successive stack of functionalized layers in order to increase the quantities of biologically active molecules; the number of functionalized layers may be between 2 and 10, preferably between 2 and 5.

According to a preferred variant embodiment of the invention, two layers of hydrophilic polymer and biologically active molecule are applied onto the biocompatible support, the first layer (placed between the support and the second layer) comprises a cell growth factor, for example VEGF in EC, and the second (outer) layer comprises an antithrombotic agent, for example, heparin in HPMC; this is a preferred variant, the stacking of these two functionalized layers could be reversed (that is to say a first layer comprising VEGF in HPMC and a second layer comprising a heparin in EC).

Advantageously, the semi-permeable membranes of the invention have very good properties of permeability to the therapeutic substances of interest produced inside the bioartificial organs and a good permeability to the nutrients for the organism which are necessary for the viability of the cells contained in the bioartificial organ.

Also very advantageously, the cells very weakly adhere to the surface of the semi-permeable membranes according to the invention.

In short, the functionalized semi-permeable membranes according to the invention have the following characteristics:
they have a cut-off between 10 000 and 50 000 Daltons, preferably between 10 000 and 30 000 Daltons, and most preferably between 10 000 and 15 000 Daltons;
they have a pore density between $10^9$ and $10^{11}$ pores/cm$^2$;
they have a thickness between 5 μm and 100 μm, preferably between 10 μm and 60 μm.

According to a first embodiment, the layers of hydrophilic polymers and of biologically active molecules may cover both faces of the biocompatible support.

In a second preferred embodiment, the layers of hydrophilic polymers and of biologically active molecules cover only one of the two faces of the biocompatible support; according to this embodiment, the face of the biocompatible support covered with hydrophilic polymers and biologically active molecules is the one located on the outer side of the bioartificial organ and which is in contact with the medium surrounding the site of implantation of this organ.

The subject of the invention is also the use of a functionalized membrane according to the invention for the production of a chamber for encapsulating secretory cells producing at least one substance of therapeutic interest.

The subject of the invention is also a chamber for encapsulating secretory cells producing at least one substance of therapeutic interest, characterized in that its walls consist of a functionalized semi-permeable membrane as defined above delimiting a space capable of containing the secretory cells producing at least one substance of therapeutic interest and a bioartificial organ comprising a chamber for encapsulating secretory cells producing at least one substance of therapeutic interest, characterized in that the walls of the encapsulation chamber consist of a functionalized semi-permeable membrane as defined above.

The use of the semi-permeable membranes according to the invention for the production of bioartificial organs leads to devices whose implantation is enhanced by the release of antithrombotic agents and the formation of blood vessels around said device during its implantation.

An encapsulation chamber according to the invention may have the characteristics of the constituent chambers of bioartificial organs described in the prior art.

Figure 1:
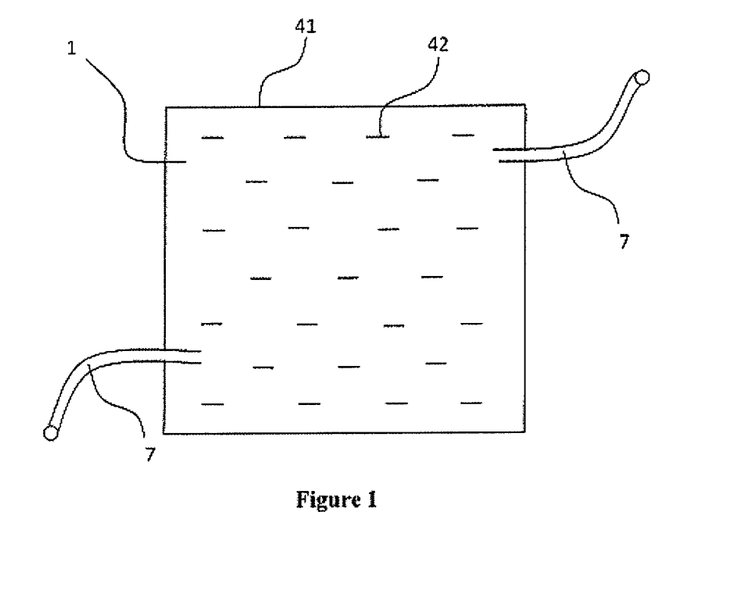
FIG. 1 represents the top view of an example of an embodiment of a bioartificial organ according to the invention.
Figure 2:
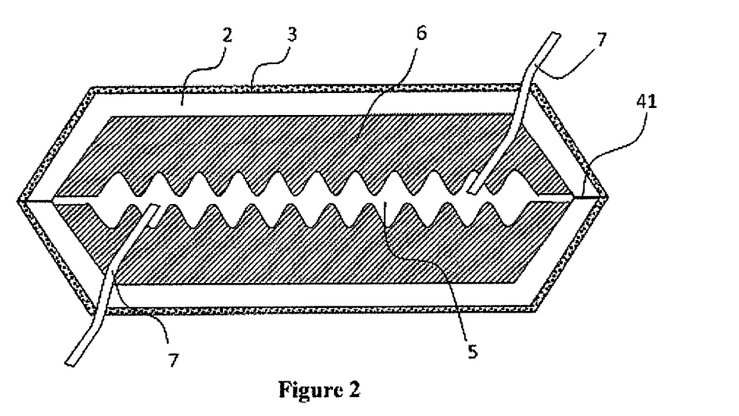
FIG. 2 represents a cross section of this same bioartificial organ; this bioartificial organ comprises an encapsulation chamber (1) having a parallelepipedal shape and two functionalized semi-permeable membranes, one at the top and one at the bottom, consisting of a biocompatible support (2) on which layers of hydrophilic polymers and biologically active molecules (3) are placed; these two semi-permeable membranes are welded along their outer edge (41) and along various points of their surface (42); the two functionalized membranes delimit the space (5) of the encapsulation chamber containing cells producing at least one substance of therapeutic interest; the space is provided with an inner matrix (6).

A non-limiting example of one embodiment of a bioartificial organ comprising an encapsulation chamber according to the invention, such a bioartificial organ is illustrated in FIGS. 1 (top view) and 2 (cross section).

According to this particular embodiment, the encapsulation chamber (1) has a parallelepipedal shape and comprises two functionalized semi-permeable membranes, one at the top and one at the bottom, consisting of a biocompatible support (2) on which layers of hydrophilic polymer and biologically active molecule (3) are placed; these two semi-permeable membranes are welded along their outer edge (41) and along various points on their surface (42).

The two functionalized membranes delimit the chamber (5) of the encapsulation chamber which contains cells producing at least one substance of therapeutic interest. The chamber is advantageously coated with an inner matrix (6). The height of the inside of the encapsulation chamber corresponds to the height of the cells or groups of secretory cells (for example in the case of pancreatic islets); by way of example, this height will be between 5 and 900 w.

The welding points (42) located at the surface of the membranes allow a better distribution of the secretory cells during the filling of the encapsulation chamber and, in particular, make it possible to avoid aggregation of the secretory cells.

Finally, according to a preferred variant, the bioartificial organ is additionally equipped with two flexible tubes (7) which make it possible to fill or empty the bioartificial organ; this is of particular advantage for replacing the contents of the bioartificial organ when it is implanted in a patient, without carrying out an explantation.

The cells producing at least one substance of therapeutic interest may be, for example, cells of the pancreatic islets (or islets of Langherans) or insulin cells obtained from cell lines such as MIN-6, RIN-m5f and INS-1, which produce insulin when the encapsulation chamber is intended for the production of a bioartificial pancreas.

The cells may also be hepatic cells when the encapsulation chamber is intended for the production of a bioartificial liver.

In a particular embodiment, the cells are transfected or transformed with at least one nucleic acid allowing the expression of a substance of therapeutic interest. Among the substances of therapeutic interest, there may be mentioned, by way of illustration, insulin, cytokines, peptide hormones, growth hormones and calcitonin.

In general, the expression substance of therapeutic interest, for the purposes of the invention, is understood to mean a substance which is released or secreted by the cell producing it and exerts its effect on a target cell or on a target molecule in the host organism, such as for example a neurotransmitter, a hormone, a growth factor or a cytokine.

A great diversity of cells may be used, including immortalized cell lines such as dividing primary cell cultures.

The cells may be, for example, myoblasts, which are precursor cells for muscle cells derived from populations of stem cells of the mesoderm, and which can be easily transformed with a nucleic acid allowing the expression of the substance of therapeutic interest. Reference may be advantageously made by a person skilled in the art, for example to the PCT applications published under the numbers WO 94/02129, WO 93/03768 and WO 90/15863.

The cells may also be beta cells of the islets of Langherans of the pancreas or hepatocytes, preferably of human origin.

The cells contained in an encapsulation chamber according to the invention may be incorporated into a matrix, such as a type IV collagen matrix, where appropriate in combination with laminin, entactin and heparan sulfate as the matrix marketed under the name Matrigel.

The cells contained in an encapsulation chamber according to the invention may generally be incorporated into a matrix composed of any product or combination of products allowing the immobilization of these cells in a viable form.

According to another aspect, the invention also relates to a bioartificial organ, characterized in that it comprises at least one encapsulation chamber as defined above.

The characteristics of a bioartificial organ according to the invention may be of any type known per se in the prior art.

For the preparation of a bioartificial organ of the invention, whose essential characteristic is that of comprising at least one chamber for encapsulating cells, equipped with a functionalized semi-permeable membrane according to the invention, reference may be advantageously made by a person skilled in the art to U.S. Pat. Nos. 5,981,211, 4,578,191, 5,837,234, 6,023,009, 5,605,835 and 4,323,457.

According to a particular embodiment of the invention, the bioartificial organ is a bioartificial pancreas containing cells of the islets of Langherans.

According to a second particular embodiment of the invention, the bioartificial organ is an artificial liver containing hepatic cells.

By way of illustration, a bioartificial organ according to the invention may be implanted intraperitoneally or above the renal capsule; it can remain implanted for at least five years, if necessary, its contents (secretory cells) can be replaced.

BRIEF DESCRIPTION OF THE DRAWINGS

Figures

The graph of FIG. 3 represents the permeability to glucose of the membranes prepared in example 1.

On the basis of the images produced after 7 days, 14 days and 1 month of implantation, several parameters characterizing the development of vascularization of the tissues surrounding the implant were evaluated, they are:
- the mean of the number of blood vessels per field counted in 5 fields of the sections after 7 days, 14 days and 1 month of implantation for the various membranes tested (FIG. 6);
- the mean distance between the semi-permeable membrane and the first blood vessels counted in 5 fields of the sections after 7 days or 1 month of implantation for the various membranes tested (FIG. 7);
- the mean diameter of the blood vessels measured in 5 fields of the sections after 7 days or 1 month of implantation for the various membranes tested (FIG. 8).

DETAILED DESCRIPTION

EXAMPLES

Example 1

Production of Semi-Permeable Membranes

I. Membranes Comprising a Support Made of Polycarbonate Covered with Hydroxypropyl Methylcellulose (HPMC) Alone (Control Membranes)

I.A. Preparation of the HPMC Solutions

The following solutions are prepared at least the day before the treatment by dissolving 2 g of HPMC (E4M from Dow Chemical) in 1 l of water for injection or an equivalent ratio in order to obtain a concentration of 0.2% HPMC. The solution is left overnight with stirring (magnetic stirrer) at room temperature.

I.B. Plasma Treatment of the Polycarbonate Supports and Coating

The support membranes made of polycarbonate Pokalon (Lonza) are cleaned beforehand with water for injection.

The treatments of the polycarbonate support membranes are carried out in a clean room with a Branson plasma machine; the following treatment is applied: Ar—50 W—10 minutes.

The polycarbonate support membranes thus treated are immediately immersed in the HPMC solution and are then allowed to dry at 45° C. in an oven.

II. Membranes Functionalized with VEGF in HPMC According to the Invention

II.A Preparation of the Solutions of HPMC and VEGF

A 0.1% HPMC solution (1 g/l) is prepared in water for injection.

1 ml of this HPMC solution is diluted in 100 ml of DPBS phosphate buffer, giving an HPMC concentration of 0.001%.

The preparation of a VEGF solution (Tebu-bio SAS) at 10 µg/ml (that is 10 mg/l) is carried out by adding 1 ml of DPBS to the vial containing 10 µg of VEGF.

The whole of this VEGF solution (that is 1 ml therefore comprising 10 µg of VEGF) is mixed with 4 ml of HPMC solution (comprising 40 µg of HPMC) in order to prepare a solution which comprises 25 parts of VEGF per 100 parts of HPMC.

The mixture is introduced into a 50 ml flask and diluted in order to obtain final concentrations of 0.2 µg/ml for VEGF and 0.8 µg/ml for HPMC.

According to the same principle, solutions comprising HPMC/VEGF ratios of 100/50 and 100/10 are prepared.

II.B Plasma Treatment and Coating

These steps are carried out as described at point I.B with the exception of the drying which is carried out at room temperature.

III. Membranes Functionalized with Heparin in Ethyl Cellulose (EC) with an EC/Heparin Ratio of 100/25 According to the Invention III.A Preparation of the Solutions The EC solution is prepared as follows: EC exists in the form of a paste (Surelease from Colorcon, at 25% that is 25 mg/100 mg); it is diluted in water for injection at 1 g/l, that is 250 mg/l of EC.

This solution is diluted a second time in water for injection in order to give a solution at 10 mg/l of EC. Commercial heparin solution (heparin Choay 25000 IU Sanofi-Aventis) has a heparin concentration of 200 mg/5 ml; it is diluted in water for injection until a heparin concentration of 10 µg/ml is obtained.

1 ml of the heparin solution (containing 10 µg of heparin) is mixed with 4 ml of the EC solution (containing 40 µg of EC) to give a solution having a ratio of 25 parts of heparin per 100 parts of EC.

This solution is introduced into a 50 ml flask and diluted in order to bring the concentrations back to 0.2 µg/ml for heparin and to 0.8 µg/ml for the EC.

III.B Plasma Treatment and Coating

These steps are carried out as described at point I.B with the exception of the drying which is carried out at room temperature.

IV. Membranes Functionalized with Heparin in EC and VEGF in HMPC According to the Invention IV.A Preparation of the Solutions The solutions of heparin in EC and of VEGF in HPMC are prepared as indicated at points III.A and II.A respectively.

IV.B Plasma Treatment and Coating

The plasma treatment is carried out as described at point I.B.

The coatings are carried out in the following order:
immersion of the polycarbonate support in the EC/heparin solution and then drying at room temperature;
then immersion of the support functionalized with heparin in the HPMC/VEGF solution and then drying at room temperature.

V. Preparation of the Device According to the Invention with a Silicone Support

Devices according to the invention may be prepared with a silicone support. These supports constitute a complementary part of the semi-permeable membranes according to the invention.

The silicone supports (Nusil) are plasma-treated beforehand under the following conditions: Ar—100 W—7.5 minutes.

Next, the application of the functionalized layers is carried out as described in the protocols of parts II, III and IV; it being possible for the water for injection to be replaced with distilled water.

Example 2

Characterization of the Permeability of the Semi-permeable Membranes

Trials for permeability to glucose and to immunoglobulins (IgG) of the preprepared membranes are carried out as follows:

Materials: diffusion chamber consisting of a top compartment and a bottom compartment separated by a membrane whose permeability it is desired to test (imperviousness between the two compartments is provided by a seal), glucose (Prolabo), NaCl (Sigma, ref. S3014), IgG (Sigma, ref. 196640), distilled water.

Preparation of the Solutions
physiological saline, per 1 liter:

| NaCl | 9 g |
| distilled water | 1 l | glucose solution, per 1 liter:

| glucose | 4 g |
| physiological saline | 1 l |

IgG solution (final concentration 5.75 µg/ml), per 100 ml:

| stock IgG (10 mg/ml) | 575 µl |
| physiological saline | 99.425 ml |

Protocol:

3 ml of physiological saline are introduced into the bottom compartment of the diffusion chamber, the membrane whose permeability it is desired to test is placed on top of the physiological saline while avoiding the presence of air bubbles.

3 ml of glucose solution are introduced into the top compartment, the diffusion chamber is closed with parafilm and is then incubated at 37° C.

For glucose: 1 ml of the solution present in the top compartment of the diffusion chamber is collected after gentle homogenization. The membrane is then removed and placed in a Petri dish and 1 ml of the solution in the bottom compartment is collected after homogenization.

The enzymatic assay of glucose is carried out with the aid of the Glucose RTU kit (BioMérieux, reference 61 269).

Figure 3:
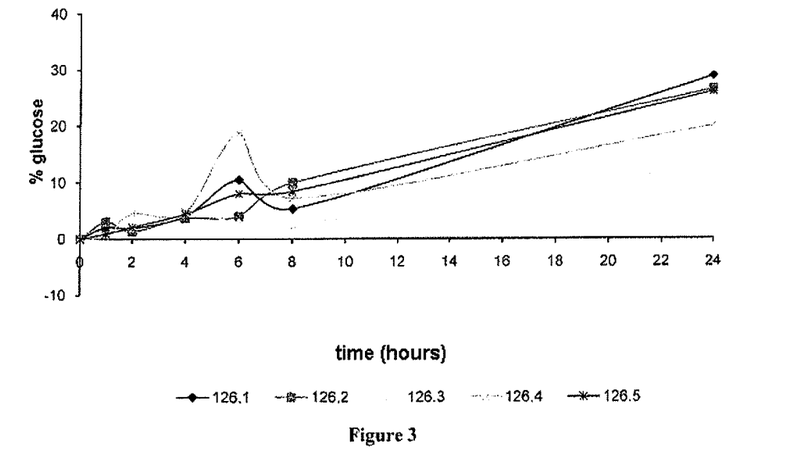

The results (expressed as glucose content in the bottom compartment as a function of time) are presented in the graph of FIG. 3.

Comparison of the permeability to glucose of the functionalized membranes according to the invention (126.3, 126.4 and 126.5) in relation to the membranes of the state of the art whose preparation is described in example 1 point I (126.1 and 126.2) demonstrates that the treatment intended to functionalize the membranes does not reduce permeability to glucose.

For the IgGs: 1 ml of the solution present in the top compartment of the diffusion chamber is collected after gentle homogenization. The membrane is then removed and placed in a Petri dish where it is rinsed with 1 ml of distilled water. The rinse water is preserved. 1 ml of the solution in the bottom compartment is collected after homogenization.

The assay of the IgGs is carried out by the Bradford method (Bradford, 1976 & Wright et al., 1996).

The semi-permeable membranes according to the invention are completely impermeable to the IgGs; they thus advantageously prevent penetration of the encapsulation chamber for cytokines and chemokines.

Example 3

Trials for Implantation of the Semi-permeable Membranes

The membranes prepared as described in example 1 are implanted into the peritoneal cavity of healthy Wistar rats.

In the remainder of the experimental part, the membranes are coded as follows:
- 126.1 and 126.2: "control" membranes (prepared as described in part I of example 1);
- 126.3: "VEGF/HPMC" membrane (ratio: 25/100, prepared as described in part II of example 1);
- 126.4: "heparin/EC" membrane (ratio: 25/100, prepared as described in part III of example 1);
- 126.5: "VEGF/HMPC+heparin/EC" membrane (for both layers, the ratio is 25/100, the membrane is prepared as described in part IV of example 1).

Male Wistar rats of 230-250 g are anesthetized with gas (isoflurane). A 3 cm laparotomy in the left iliac fossa allows the implantation of the membrane. The incision is then closed. The rats are then placed in cages with food and water ad libitum (each membrane is implanted in three rats).

After one week, the rats are anesthetized with an Imalgene/Rumpun mixture, and incised in order to recover the membrane and the epiploic tissue surrounding it. The membrane is then placed in 2.5% glutaraldehyde while the tissue is fixed in 3% paraformaldehyde prepared in a PBS buffer for 3 h.

The epiploic tissue collected is embedded in paraffin for histological analysis according to the following protocol:

I. Sampling

I.1. Materials

Solutions
- 1 flask of 500 ml of 36% formaldehyde (reference SIGMA—F8775—500 mL).
- 1 flask of 500 g of powdered paraformaldehyde (reference: SIGMA—30525-89-4) which should be stored in a refrigerator.
- 1 flask of 10 ml of 25% glutaraldehyde (reference: SIGMA—G5882—10×10 mL)
- 1 flask of 500 mL of PBS (reference: GIBCO—14190-094).
- 1 flask of 500 mL of PBS X10 (reference: GIBCO—14200-067).

I.2. Preparation of the Solutions

Because of the toxicity of the products used, the following steps are carried out in a safety cabinet with gloves.

I.2.1. Solution of Formaldehyde at 3%

Formaldehyde makes it possible to preserve the tissue surrounding the membrane during collection for 4 h maximum; it is also used for the eosin/hematoxin stainings.
- in a 100 mL flask, put 100 mL of PBS;
- add 8.3 ml of formaldehyde at 36%;
- mix.

I.2.2. Solution of Paraformaldehyde at 8%

The solution of paraformaldehyde at 4% may be used in place of the formaldehyde solution; it makes it possible to fix the tissues up to 24 h and is used for the immunocytochemical staining.
- Prepare an alkaline solution by dissolving 1 sodium hydroxide pellet in 2 to 3 mL of distilled water;
- put 8 g of paraformaldehyde in suspension in 100 mL of distilled water;
- in a safety cabinet, heat the suspension on a heating magnetic stirrer;
- when the suspension simmers (at about 80° C.), add a few drops of alkaline solution until the mixture becomes completely clear;
- rapidly cool in ice.

This solution should be used immediately or stored at −20° C. in 20 mL fractions ready to use.

The paraformaldehyde solution at 4% is prepared by dilution with PBS (introduction of 20 ml of paraformaldehyde solution at 8% into 20 ml of PBS and then mixing).

I.2.3. Solution of Glutaraldehyde at 2.5%

In a 100 mL flask, put 100 mL of distilled water.

Add 10 mL of glutaraldehyde at 25%.

Glutaraldehyde makes it possible to preserve the membrane collected.

II. Incorporation into Paraffin

II.1. Materials
- 1 flask of 500 mL of PBS (reference: GIBCO—14190-094).
- 1 flask of 500 mL of PBS X10 (reference: GIBCO—14200-067.
- 1 bottle of 1 L of toluene (reference: FISHER SCIENTIFIC—code: T/2250/17), toluene is very toxic and volatile and should be stored and handled in a safety cabinet.
- 1 bottle of 1 L of 70% ethanol.
- 1 bottle of 1 L of 95% ethanol.
- 1 bottle of 1 L of 100% ethanol.
- Paraffin (reference: TYCO/HEALTHCARE—ref: 8889501006).
- 1 standard cassette for incorporation HISTOSETTE 2 (reference: M.492, ref 039753 or M.485, ref 039775 in the Dutscher catalog).
- 1 dish for incorporation 37×24 mm (reference: RICHARD ALLAN SCIENTIFIC—catalog No. 58953)
- 3 beakers of 50 mL.
- 2 beakers of 600 mL.
- 1 pair of forceps.
- Aluminum.
- Rubber gloves.

II.2. Solutions

II.2.1. PBS

In an empty PBS flask (500 mL), put 50 mL of PBS X10; adjust with 450 mL of distilled water; mix.

II.2.2. Ethanol at 70%
In a 1 L bottle, put 700 mL of ethanol;
adjust with 300 mL of distilled water;
mix.

II.2.3. Ethanol at 95%
In a 1 L bottle, put 950 mL of ethanol;
adjust with 50 ml of distilled water;
mix.

II.2.4. Paraffin
In the 2 beakers of 600 mL, pour the paraffin pellets;
place the 2 beakers at 62° C.-65° C. in the oven in the histology room;
keep the beakers in the oven.

II.3. Preparation of the Workstation
On the worktop: place 9 containers comprising the solutions in the following order: 2 PBS containers and 7 ethanol containers.

In the chemical safety cabinet, place 3 beakers of 50 mL of toluene and in the oven, place 3 paraffin containers.

II.4. Baths
The tissues collected are treated according to the following steps:

| STEPS | SOLUTIONS | CONDITIONS |
| --- | --- | --- |
| Fixing | 3% formalin in PBS | 2 hours mini-4 h maxi, at room temperature |
| Washes | PBS | 2 × 10 min |
| Dehydration | 70% alcohol | 2 × 10 min |
|  | 95% alcohol | 3 × 15 min |
|  | 100% alcohol | 2 × 30 min |
| Impregnation | toluene | 3 × 15 min |
| Incorporation | paraffin | 3 × 20 min |

II.5. Incorporation of the Tissue into Paraffin
Pour liquid paraffin into the incorporation dish;
put the tissue to be incorporated in the dish;
apply the incorporation cassette and pour the paraffin over it for a uniform covering;
allow to cool for a few minutes at room temperature, and then place in a refrigerator for 24 h minimum.

III. Preparation of the Sections
III.1. Materials
Incorporation cassette
Microtome
Permafrost slides 75×25 mm (reference: 045796, in the Dutscher catalog).
1 disposable transfer pipette
1 container containing distilled water
2 brushes: 1 large brush+1 fine brush
2 tools for collecting the sections
Slide heater
1 bottle of 1 L of 95% ethanol
1 bottle of 1 L of 100% ethanol
1 bottle of toluene (reference: FISHER SCIENTIFIC—code: T/2250/7
5 Hellendahl type staining tanks
Rubber gloves.

III.3. Microtome Sections
The sections are produced with the aid of the Leica RM2265 microtome according to the recommendations of the manufacturer.

III.4. Paraffin Removal
This step makes it possible to remove the paraffin present on the slide while preserving the tissue, the slide is treated with the following baths:

| TOLUENE | 2 × 15 min |
| --- | --- |
| 100% ALCOHOL | 2 × 10 min |
| 95% ALCOHOL | 1 × 5 min |
| TAP WATER | rapid passage |
| DISTILLED WATER | rapid passage |

IV. Staining
IV.1. Materials
Permafrost slide 76×26 mm, with the fixed section.
1 bottle of 1 L of eosin.
1 bottle of 1 L of alcohol-acid.
1 bottle of 1 L of ammonia water.
1 flask of harris hematoxylin (reference: SURGIPATH—01562$^E$).
1 bottle of 500 mL of 100% ethanol.
1 toluene bath.
1 tube of adhesive (reference: EUKITT).
cover glass 25×75 mm (reference: ESCO No. 2951).
13 tanks with lids (reference: 068506, in the Dutscher catalog p. 187).
2 baskets (reference: 068507, in the Dutscher catalog p. 187).
Absorbent paper.
Rubber gloves.
1 coffee filter.

IV.2. Preparation of the Solutions
IV.2.1. Eosin Solution (1 l)
In a 1 L bottle, put:
eosin 225 RA2: 3.125 g (reference: REACTIF RAL—312730-0100);
erythrosine RA2: 1.875 g (reference: REACTIF RAL—312820-0100);
distilled water: 1 L
Mix and filter with the aid of the coffee filter.

IV.2.2. Solution of Alcohol-Acid (1 l)
In a 1 L bottle, put:
96% alcohol: 990 mL;
hydrochloric acid (HCl): 10 mL (reference: PROLABO—20.246.298) (to be handled with gloves and safety goggles)

IV.2.3. Solution of 96% Ethanol (1 l)
In a 1 L bottle, put 960 mL of pure ethanol;
adjust with 40 mL of distilled water and mix.

IV.2.4. Solution of 0.20% Ammonia Water (1 l)
In a 1 L bottle, put:
20% ammonium hydroxide 2.5 mL (ref.: FISHER SCIENTIFIC—Code; A/3367/17)
distilled water: 1 L
and then mix.

IV.3. Staining Protocol
The staining of the tissues is carried out using successive baths:
immersion in harris hematoxylin for 1 minute and 30 seconds;
two baths in water;
immersion in the alcohol-acid solution with stirring two to three times;
two baths in water;
immersion in ammonia water until the tissue becomes blue;
one bath in water;
immersion in eosin for 10 seconds;
one bath in ammonia water;
3 successive baths in 96% ethanol;
final bath in toluene The baths in water and ethanol consist of 2-3 rapid stirrings.

After the baths:

apply the adhesive to the tissue taking care not to damage it;

apply the cover glass and press well in order to remove any air bubbles;

roughly remove excess adhesive;

rapidly dip the slide in toluene and immediately remove it;

wipe with absorbent paper taking care not to move the cover glass;

repeat the operation 2 to 3 times until complete removal of the adhesive residues is obtained.

IV.4. Role of the Various Solutions

The Harris hematoxylin allows red-violet staining of the basophilic elements of the tissue.

The alcohol-acid allows mild destaining and the production of an orange tint.

The 0.20% NH4 ammonia water allows violet staining of the cell nuclei.

The eosin allows orange-pink staining of the acidophilic elements of the tissue.

The 3 96% ethanol baths allow destaining to be carried out.

The toluene bath makes it possible to fix the tissue and to remove the excess dye.

The counting of the blood vessels, the measurement of their diameter and the determination of the distance between the module and the first blood vessels are carried out under a binocular lens with the aid of a micrometer; 5 fields are counted for each section at the rate of three sections per tissue.

V. Results

Figure 4:
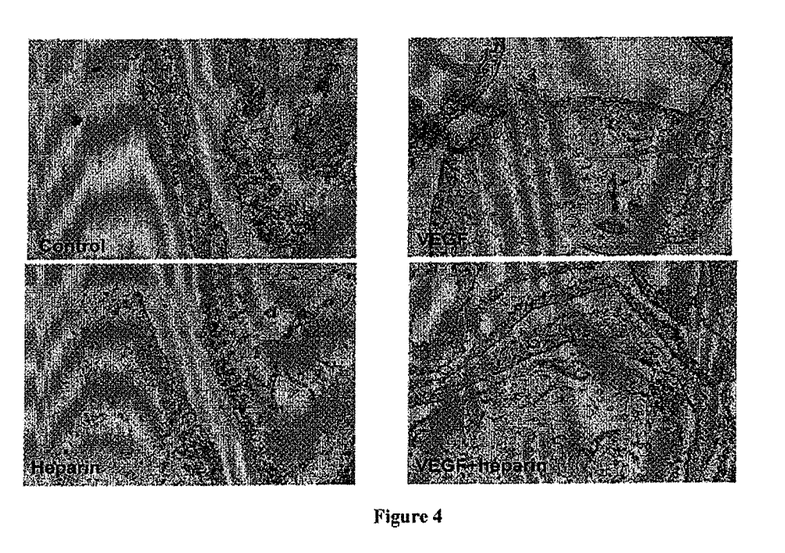
FIGS. 4 and 5 are images of histological sections of the epiploic tissue surrounding the membrane: with no biologically active molecule, with heparin, with VEGF and with heparin and VEGF, after 7 days (FIG. 4) or 1 month (FIG. 5) in rats (×400).
Figure 5:
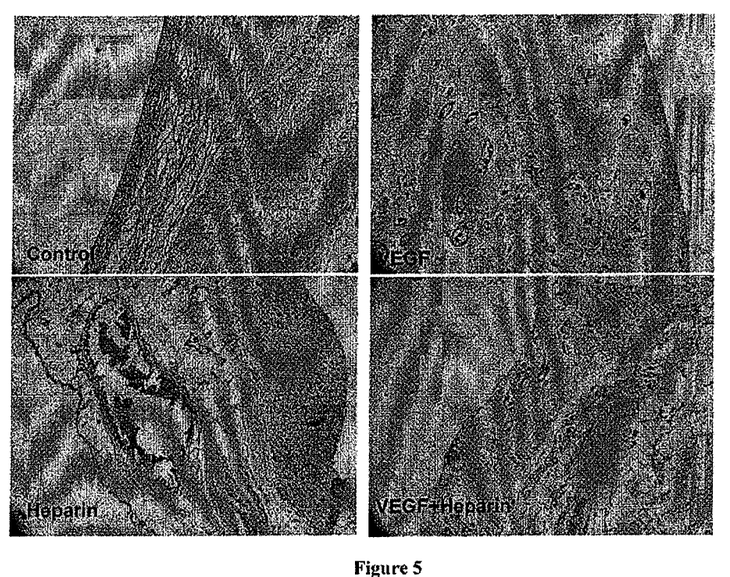

The images of the sections prepared 7 days or 1 month after the implantation of the membranes are reproduced in FIGS. 4 and 5.

Figure 6:
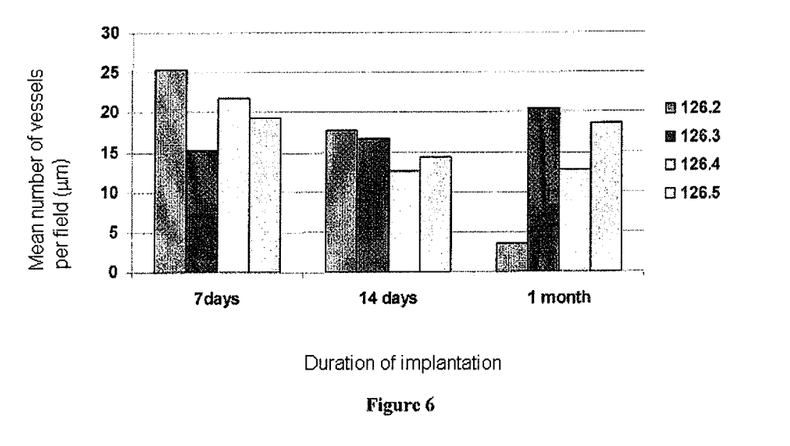

FIG. 6 represents the mean of the number of blood vessels counted in 5 fields of the sections after 7 days, 14 days or 1 month for the various membranes tested.

Figure 7:
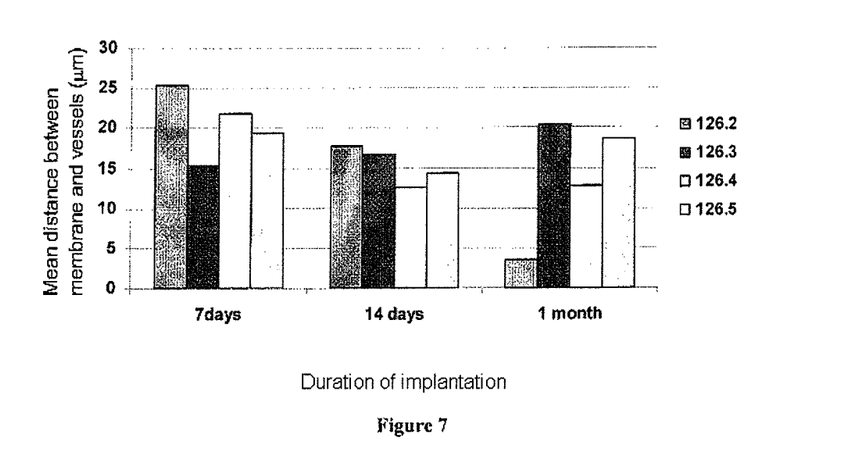

FIG. 7 represents the mean distance between the semipermeable membrane and the first blood vessels counted in 5 fields of the sections after 7 days or 1 month for the various membranes tested.

Figure 8:
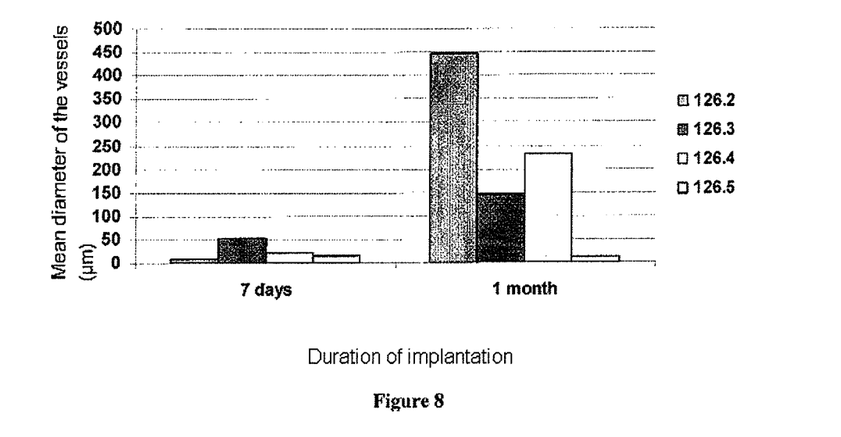

FIG. 8 represents the mean diameter of the blood vessels measured in 5 fields of the sections after 7 days or 1 month for the various membranes tested.

These trials show that VEGF induces a long-term formation of blood vessels. Heparin also exhibits a vascularization-inducing effect.

It is interesting to note that these two compounds have a synergistic effect.

The invention claimed is:

1. A functionalized semi-permeable membrane for production of a chamber for encapsulating secretory cells of a bioartificial organ composed of a porous biocompatible support, wherein:

said porous biocompatible support is pretreated so that its surface energy is greater than or equal to 50 mJ·m$^{-2}$;

pores of said porous biocompatible support have an inner size between 5 and 100 nm, and said functionalized semi-permeable membrane comprises at least two layers each comprising a hydrophilic polymer and at least one biologically active molecule.

2. The functionalized semi-permeable membrane as claimed in claim 1, wherein the hydrophilic polymer is chosen from cellulose compounds, polyacrylamides and their copolymers, polyvinylpyrrolidone (PVP) and its copolymers, polyvinyl alcohols, copolymers of vinyl acetate, polyethylene glycols, polypropylene glycols, hydrophilic poly(meth)acrylates, polysaccharides, hyaluronic acid-based polymers and chitosans.

3. The functionalized semi-permeable membrane as claimed in claim 1, wherein the biologically active molecule is chosen from anti-inflammatory agents, anti-infective agents, anesthetics, growth factors, angiogenesis-stimulating and/or vascularization-inducing agents, wound-healing agents, immunosuppressive agents, antithrombotic agents including antiaggregation agents and anticoagulating agents, inhibitors of angiotensin-converting enzyme (ACE), or molecules stimulating insulin secretion.

4. The functionalized semi-permeable membrane as claimed in claim 1, wherein the functionalized semi-permeable membrane comprises at least two layers of hydrophilic polymer, each layer comprising at least one biologically active molecule, a first of said layers is placed between said support and a second layer and comprises a cell growth factor and the second of said layers comprises an antithrombotic agent.

5. The functionalized semi-permeable membrane as claimed in claim 4, wherein said cell growth factor is VEGF and in that said antithrombotic agent is heparin.

6. A chamber for encapsulating secretory cells producing at least one substance of therapeutic interest, characterized in that its walls consist of a functionalized semi-permeable membrane as claimed in claim 1 delimiting a space capable of containing the secretory cells producing at least one substance of therapeutic interest.

7. A bioartificial organ, wherein the organ comprises at least one encapsulation chamber as claimed in claim 6.

8. The bioartificial organ as claimed in claim 7, wherein the organ is a bioartificial pancreas containing cells of the pancreatic islets.

9. The functionalized semi-permeable membrane as claimed in claim 2, wherein the biologically active molecule is chosen from anti-inflammatory agents, anti-infective agents, anesthetics, growth factors, angiogenesis-stimulating andor vascularization-inducing agents, wound-healing agents, immunosuppressive agents, antithrombotic agents including antiaggregation agents and anticoagulating agents, inhibitors of angiotensin-converting enzyme (ACE), or molecules stimulating insulin secretion.

* * * * *